US010258514B2

(12) United States Patent
Wojtanowski (10) Patent No.: US 10,258,514 B2
(45) Date of Patent: Apr. 16, 2019

(54) REUSABLE CLOTH DIAPERS THAT CAN BE CLOSED SHUT WHEN SOILED TO CONTAIN WASTES WITH A THIN INSERT THAT CAN ABSORB A DEFINED AMOUNT, IS CONTOURED, AND CAN EASILY BE GUIDED INTO A DIAPER

(71) Applicant: Melissa Dawn Wojtanowski, Los Alamitos, CA (US)

(72) Inventor: Melissa Dawn Wojtanowski, Los Alamitos, CA (US)

(73) Assignee: Melissa Wojtanowski, Los Alamitos, CA (US)

( * ) Notice: Subject to any disclaimer, the term of this patent is extended or adjusted under 35 U.S.C. 154(b) by 905 days.

(21) Appl. No.: 14/628,296

(22) Filed: Apr. 23, 2015

(65) Prior Publication Data
US 2016/0000614 A1 Jan. 7, 2016

(51) Int. Cl.
*A61F 13/49* (2006.01)
*A61F 13/505* (2006.01)

(52) U.S. Cl.
CPC .. *A61F 13/49004* (2013.01); *A61F 13/49058* (2013.01); *A61F 13/505* (2013.01)

(58) Field of Classification Search
CPC .......... A61F 13/49003; A61F 13/49004; A61F 13/49058; A61F 13/4906; A61F 13/505; A61F 2013/49063; A61F 13/493; A61F 13/539; A61F 2013/49082; A61F 2013/49093; A61F 2013/5055
See application file for complete search history.

(56) References Cited

U.S. PATENT DOCUMENTS

| | | | | |
|---|---|---|---|---|
| 4,425,130 A | * | 1/1984 | DesMarais | A61F 13/474 604/358 |
| 4,453,938 A | * | 6/1984 | Brendling | A61F 5/4401 383/113 |
| 5,019,068 A | * | 5/1991 | Perez | A61F 13/66 604/386 |
| 5,069,672 A | * | 12/1991 | Wippler | A61F 13/62 604/385.14 |
| 2008/0215027 A1 | * | 9/2008 | Labit | A61F 13/49004 604/378 |
| 2012/0116340 A1 | * | 5/2012 | Labit | A61F 13/15268 604/377 |
| 2013/0190712 A1 | * | 7/2013 | Vaughan | A61F 13/49004 604/385.14 |
| 2015/0282996 A1 | * | 10/2015 | Newton | A61F 13/4915 604/385.14 |

* cited by examiner

*Primary Examiner* — Kristen Matter (57) ABSTRACT

According to various aspects, exemplary embodiments are provided of reusable cloth diapers. In the diaper is an insert in which there are inner absorbing layers that are arranged specifically to absorb and hold a predetermined volume of waste. Also, the layers are sewn on three sides leaving a pocket opening that allows a person to easily guide their hand into the insert to easily guide and place into position inside the reusable cloth diaper.

3 Claims, 9 Drawing Sheets

REUSABLE CLOTH DIAPERS THAT CAN BE CLOSED SHUT WHEN SOILED TO CONTAIN WASTES WITH A THIN INSERT THAT CAN ABSORB A DEFINED AMOUNT, IS CONTOURED, AND CAN EASILY BE GUIDED INTO A DIAPER

BACKGROUND

Inserts absorb and hold the waste when a diaper is soiled. Usually they are sewn to the inner layer of a cloth diaper, laid into the diaper, or stuffed into an opening inside the diaper. Disadvantages of an insert permanently sewn to the inner layer that is one size include that when on a baby the size and amount of waste changes as they grow. This presents issues including the diaper insert being too bulky which can make movement difficult for a small baby that does not really need all the extra absorbency capability of the bigger insert to even a leaky insert that cannot hold enough waste of a larger baby with increased absorbency needs. The sewn-in insert takes on a one size fits all approach but a growing baby and even different babies have more individualized needs at various times of growth where this one size approach is not accommodating.

Another disadvantage of inserts currently on the market is that the inserts can become rather bulky especially as the baby grows bigger in size due to the fact that bulky materials can be used and or the materials have a low absorbency in relation to the thickness of the materials used.

Another disadvantage to inserts stuffed into a pocket opening type reusable diaper, for example, is that it can be difficult to guide the insert, get it to lay flat inside the pocket, or get it to lay in the right spot especially if more than one insert is needed to absorb the wastes.

Reusable diapers on the market cannot be held shut in any manner to contain wastes. This can especially be a nuisance when more than one insert is needed to hold the waste, a large amount of stool is present, or when you are not at home but at a store shopping, for example. Diapers can be rolled up if the inserts are not too bulky. However, the diapers can easily fall open. This can be difficult when on the go and out and about or with a messy stool. Other disadvantages of diapers that cannot be closed up until they are ready to be cleaned include sanitary and risk of possible contamination of wastes with other objects that could potentially come in contact with a diaper that easily falls open. Cleanliness and sanitation become an issue when using reusable cloth diapers.

SUMMARY

In accordance with an outer side of a reusable cloth diaper they generally comprise at least one embroidered design containing a female fastener and when rolled closed keeps the diaper shut by fastening using the male fastener positioned on inner side of reusable cloth diaper having an additional female fastener directly neighboring on the outer side of the reusable cloth diaper, male fastener positioned on the inner side without any female fastener directly neighboring on the outer side, and the additional female fastener.

ADVANTAGES

Accordingly several advantages of one or more aspects are as follows: to provide an insert that can be matched closely to the actual absorbency needs of a particular baby, the insert being contoured for increased comfort and ease of movement between the inner thighs, the insert containing a pocket opening that can be easily guided into the diaper to hold the wastes, to decrease the risk of contamination and for sanitary purposes. These and other benefits of one or more aspects will become apparent from a consideration of the ensuing description and accompanying drawings.

DRAWINGS

FIGS. 1A-1F and 2E reusable cloth diaper that can be easily rolled up and closed shut when soiled.

FIGS. 2A-2G shows the basic structure of an insert in which:

FIG. 2F shows the general view for 2G a perspective sectional. 2G shows the at least one second inner absorbing layer (30) and the at least one inner absorbing layer (24) both sewn to outer layer fabric #1 (26) to create the first finished edge at the pocket opening.

---

Drawings---Reference Numerals

| | |
|---|---|
| 2 outer side of reusable cloth diaper | 4 inner side of reusable cloth diaper |
| 6 embroidered design | 8 female fastener on embroidered design |
| 12 male fastener positioned on inner side of reusable cloth diaper having an additional female fastener directly neighbouring on the outer side of the reusable cloth diaper | |
| 13 male fastener positioned on the inner side without any female fastener neighbouring on the outer side | |
| 14 front waistline | 16 back waistline |
| 18 additional female fastener | 20 insert |
| 24 inner absorbing layer(s) | |
| 26 outer layer fabric #1 | 28 pocket opening |

-continued

| Drawings---Reference Numerals | |
|---|---|
| 30 the at least one second inner absorbing layer | 32 outer layer fabric #2 |

DETAILED DESCRIPTION—FIGS. IA-1F and 2E

Reusable cloth diapers include but are not limited to the following baby diapers called: all in ones, pocket cloth diapers, diaper covers, all in twos, or any other terminology relating to baby reusable cloth diapers. In addition, other reusable cloth diapers used for purposes other than babies include but are not limited to dogs and other animals, children, and adults. In one type of reusable cloth diaper for babies and the one used in this disclosure involves an outer covering made of PUL, polyurethane laminate, which is a polyester fabric laminated with a waterproof polyurethane fabric.

Figure 1A:
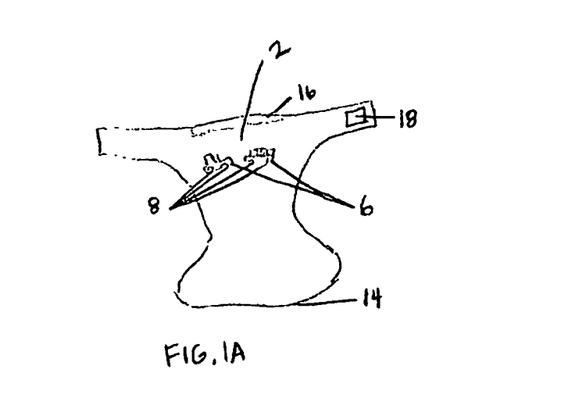
Figure 1B:
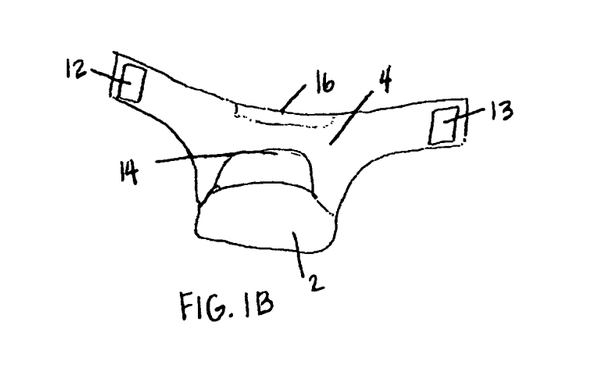
Figure 1C:
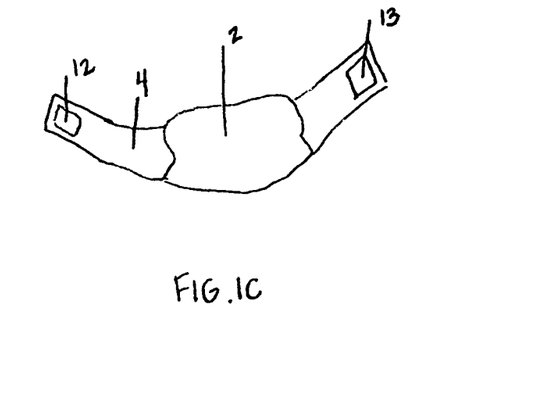
Figure 1D:
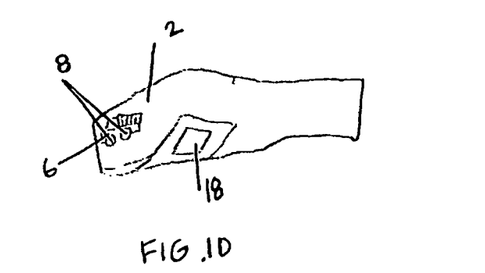
Figure 1E:
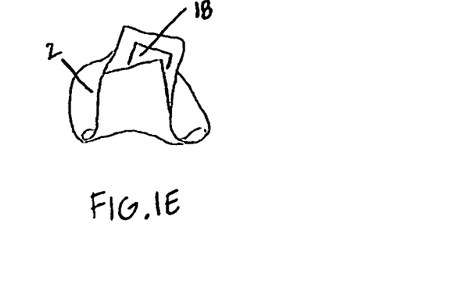
Figure 1F:
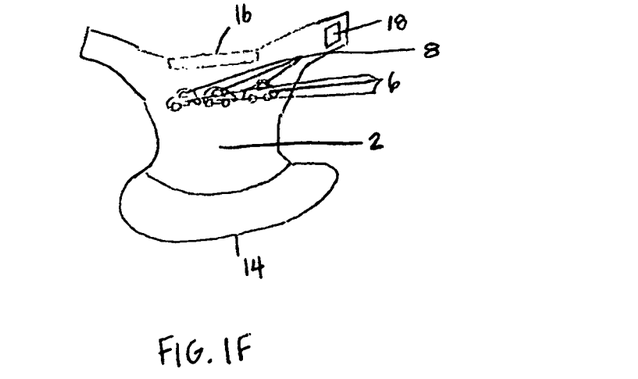
Figure 2A:
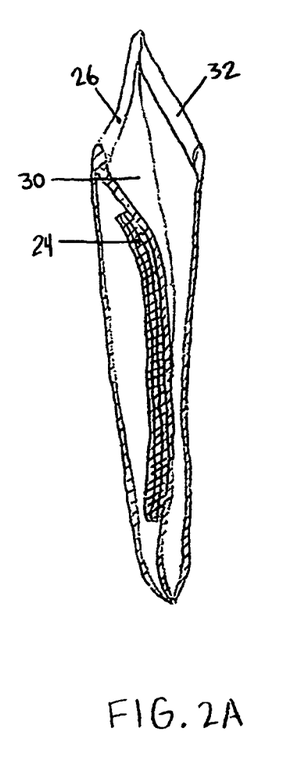
FIG. 2A shows a sectional view of the insert of FIG. 2C taken at the sectioning plane and in the direction indicated by section lines 2A-2A.
Figure 2B:
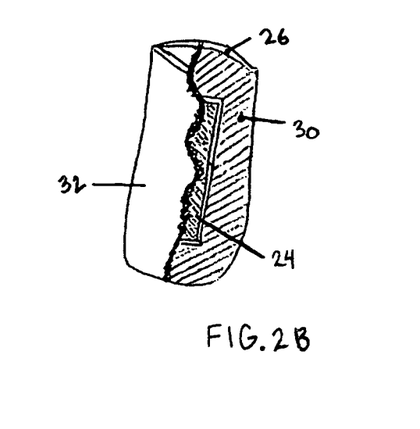
FIG. 2B shows a partial sectional view showing the basic interior structure of an insert.
Figure 2C:
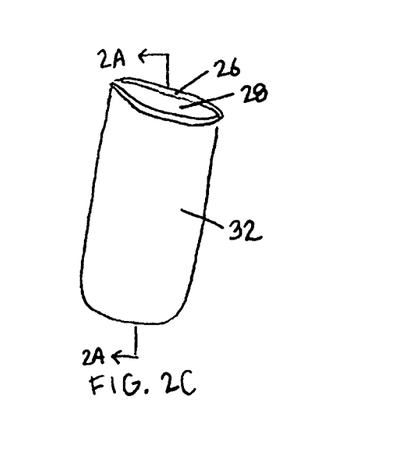
FIG. 2C perspective view showing the basic outer structure of a fully assembled absorbent insert.
Figure 2D:
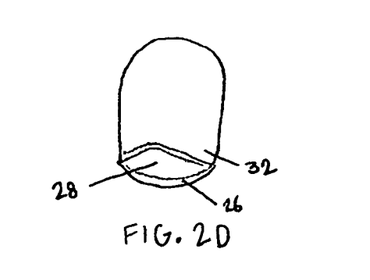
FIG. 2D is a perspective view showing a fully assembled insert pocket opening.
Figure 2E:
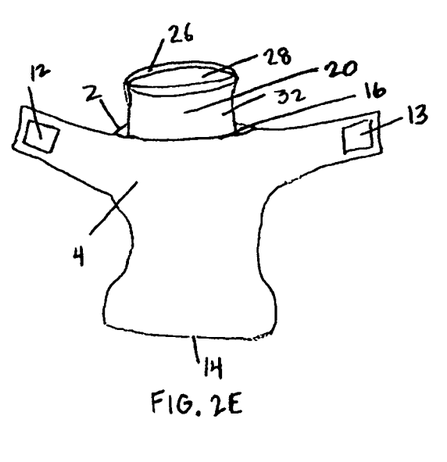
FIG. 2E is a perspective view of the inner side of a reusable diaper showing a fully assembled absorbent insert being guided half-way in between an inner layer and outer layer of an exemplary type reusable diaper.
Figure 2F:
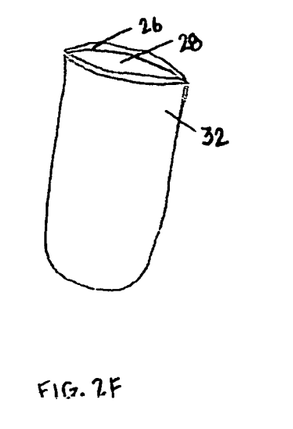

Now referring to FIGS. 2E, 1B, and 1C. When soiled, the inner side of reusable cloth diaper, (4) laid flat and facing upwards, is rolled closed starting from the front waistline to the back waistline (14) towards the back waistline (16) along with the insert. The inner side of a reusable cloth diaper is defined as the side facing inwards against the wearer when the diaper is put on and worn. The outer side of a reusable cloth diaper is defined as the side facing outwards on the wearer when the diaper is put on and worn. The front waistline is defined as the area enclosing around the front waistline of the wearer when the diaper is put on and worn. The back waistline is defined as the area enclosing around the back waistline of the wearer when the diaper is put on and worn. Referring now to FIGS. 1A, 1C, 1D, 1E, IF illustrates a soiled diaper being closed shut to contain wastes. To start, there are basically two kinds of adapters, male fasteners and female fasteners. Both fasteners are needed to fasten anything closed. On the outer side of any type reusable cloth diaper (2) there will be at least one embroidered design (6). An embroidered design is defined as being on the outer side of the reusable cloth diaper, and not limited to a specific area or section of the diaper. Somewhere on the at least one embroidered design (6) is a female fastener on the at least one embroidered design (8). A female fastener on the embroidered design is defined as a female side somewhere in or on the embroidered design to function in releasably attaching to (12) the male fastener positioned on inner side of reusable cloth diaper having an additional female fastener directly neighboring on the outer side of the reusable cloth diaper. Examples of various embroidered designs (6) are shown in FIGS. 1A and 1F containing female fasteners on the embroidered designs (8). One additional female fastener (18) is positioned on the outer side of the reusable cloth diaper (2). The additional female fastener is defined as the female side left exposed after (12) the male fastener positioned on inner side of reusable cloth diaper having an additional female fastener directly neighboring on the outer side of the reusable cloth diaper is releasably attached to the female fastener on embroidered design. In this particular disclosure, the one additional female fastener (18) is available from Velcro brand, called loop tape. One male fastener is positioned on the inner side of the reusable cloth diaper having an additional female fastener directly neighboring on the outer side of the reusable cloth diaper (12). A second male fastener is positioned on the inner side without any female fastener neighboring on the outer side (13). The second male fastener positioned on the inner side without any female fastener neighboring on the outer side (13) is defined as being releasably attachable to the additional female fastener to aid in closing the diaper shut when soiled. Both male fasteners in this particular disclosure are available from Velcro brand, called hook tape.

Then, in FIGS. 1C and 1D the male fastener (12) positioned on inner side of reusable cloth diaper having an additional female fastener directly neighboring on the reusable cloth diapers outer side (18) is attached to female fastener on the embroidered design (8). Lastly, as illustrated in FIG. 1E, the male fastener (13) positioned on the inner side without any female fastener neighboring on outer side is closed over the exposed additional female fastener (18). All of the various male fasteners and female fasteners are not limited to what is used in this particular disclosure but can also include any other items fastening similarly including snaps, various fabrics, and any other materials.

FIGS. 2A-2G BASIC EMBODIMENT of any insert.

The insert in this disclosure is guided into an opening created between an outer side reusable cloth diaper (2) and inner side reusable cloth diaper (4) of an exemplary type reusable cloth diaper at the back waistline (16). All inserts have similar structure and work in the same manner to absorb wastes. They differ only in materials and amounts used to provide a specific arrangement to absorb a predetermined volume of waste. A specific arrangement is defined as an insert composition containing very specific materials and sizes for the at least one inner absorbing layer (24), second inner absorbing layer (30), outer layer fabric #1 (26), and outer layer fabric #2 (32).

Other examples of various uses of an insert in different items include: being laid directly into a waterproof diaper cover for a baby, in a dog diaper for a puppy potty training or an older dog that has accidents, laid directly into the inside of toddler underwear to aid in potty training in case there is a mess. When used in toddler underwear, they offer protection in case the toddler unintentionally has an accident while potty training. With the inserts being constructed thinly and corning in various sizes that absorb various volumes, the toddler can potty train in comfort with plenty of protection in case there is an accident. However, there can be many other ways these inserts can be used and are not limited to the ways used in this disclosure or given as examples in this present disclosure.

Figure 2G:
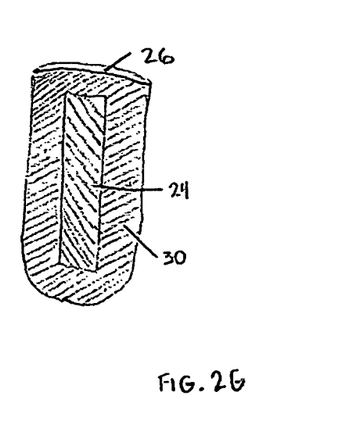
FIG. 2G is a perspective sectional view with outer layer fabric #2 removed showing the inside construction. The at least one inner absorbing layer being centered and arranged with longest sides parallel to the at least one second inner absorbing layer and sewn.

Now referring to FIGS. 2A, 2B and 2G, an inserts basic structure includes centering and arranging longest sides of the at least one inner absorbing layers (24) parallel to the longest side of at least one second inner absorbing layer (30). Then, the at least one inner absorbing layer (24) is sewn at its edge to the at least one second inner absorbing layer (30). Now referring to FIGS. 2A and 2O, outer layer fabric #1 (26) is matched to the at least one second inner absorbing layer (30) with the at least one inner absorbing layer sandwiched between. Then, on the top straight edge, outer layer fabric #1 (26) is folded over ½ inch onto the at least one second inner absorbing layer (30) with the at least one inner absorbing layer sandwiched between and sewn to create a first finished edge. Note that the at least one inner absorbing layer (24) are sandwiched between the at least one second inner absorbing layer (30) and outer layer fabric #1 (26). The reason for the latter configuration is that the at least one inner absorbing layer (24) will not be sticking out when the pocket opening is created. Next, a second finished edge at the pocket opening is created on the top straight edge, outer layer fabric #2 (32) is folded over ½ inch and sewn or basted down. Outer layer fabric #1 (26) and outer layer fabric #2 (32) are matched and put together with the at least one second inner absorbing layer (30) having the at least one inner absorbing layer (24) both sandwiched between them. Now referring to FIGS. 2C, 2D, and 2F, all unfinished edges of the U shape are sewn together while the first and second finished edges are left un-sewn. This will create the pocket opening. The pocket opening (28) allows ones hand to be slid into the insert, like a glove, to allow it to be guided and positioned into particular diaper types easily. Fabrics and sizes are not limited to what is used in the various embodiments and disclosure, but instead can include any other fabrics or materials of choice that maintain a specific arrangement to absorb a predetermined volume of waste for the consumers particular needs or use. For instance, hemp, microfiber terry, bamboo, non-woven bamboo viscose, or wood pulp.

FIGS. 3-6 Additional Embodiments of FIG. 2A-2G Basic Structure

Additional embodiments are shown in FIGS. 3, 4, 5, and 6; in each case the outer layer fabric #2 (32) is shown partially peeled back from where it is normally sewn down. There are various possibilities of fabrics and sizes of fabrics used to absorb specific predetermined volumes of waste. The latter is important, for example, since a 10 pound baby would be more comfortable in a smaller insert that could hold their smaller volume of waste. In this manner inserts are more size specific making cloth diapering more comfortable.

Figure 3:
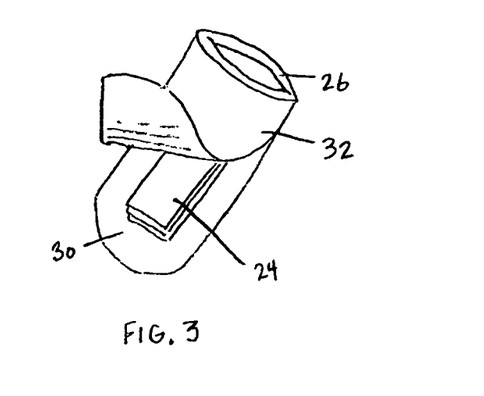
FIG. 3 shows an Organic Sherpa Size Small baby cloth diaper insert that is capable of absorbing a maximum of ⅓ cup liquid waste that commonly fits babies from birth-16 months.

FIG. 3, shows an insert called a Size Small Sherpa Insert. Its specific arrangement is currently being used for a baby cloth diaper insert and it absorbs a maximum of ⅓ cap liquid waste. It commonly fits babies up to 16 months. In this particular example, center and arrange longest sides of three 3"×8" inner absorbing layers of synthetic microfiber terry 325-350 GSM (24) parallel to the longest side of second inner absorbing layer 11"×6" of synthetic microfiber terry 325-350 GSM (30). Then, the three 3"×8" inner absorbing layers made of synthetic microfiber terry 325-350 GSM (24) are sewn at their edge to the 11"×6" synthetic microfiber terry 325-350 GSM second inner absorbing layer (30). Outer layer fabric #1 is 100% organic cotton sherpa 11"×6" weight 280 GSM (26) and is matched to 11"×6" synthetic microfiber terry 325-350 GSM second inner absorbing layer (30) with the three 3"×8" inner absorbing layers made of synthetic microfiber terry 325-350 GSM (24) sandwiched between. Then, on the top straight edge, outer layer fabric #1 100% organic cotton Sherpa 11"×6" weight 280 GSM (26) is folded over ½ inch onto the 11"×6" synthetic microfiber terry 325-350 GSM second inner absorbing layer (30) with the three 3"×8" synthetic microfiber terry 325-350 GSM inner absorbing layers sandwiched between and sewn to create a first finished edge. Next, a second finished edge at the pocket opening is created on the top straight edge. Outer layer fabric #2 100% organic cotton sherpa 11"×6" weight 280 GSM (32) is folded over ½ inch and sewn down. Outer layer fabric #1 100% organic cotton sherpa 11"×6" weight 280 GSM (26) and outer layer fabric #2 100% organic cotton sherpa 11"×6" weight 280 GSM (32) are matched and put together with the second inner absorbing layer 11"×6" synthetic microfiber terry 325-350 GSM (30) and the three 3"×8" inner absorbing layers made of synthetic microfiber terry 325-350 GSM (24) sandwiched between them. All unfinished edges creating a U shape are sewn together while the first and second finished edges are left un-sewn. This will create the pocket opening.

Figure 4:
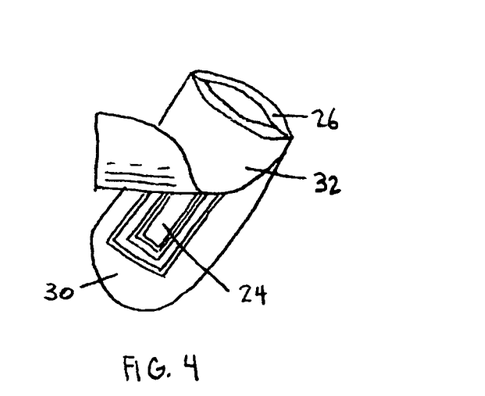
FIG. 4 shows an Organic Sherpa Size Large baby cloth diaper insert that is capable of absorbing a maximum of ⅔ cup liquid waste that commonly fits babies 16 months-potty training.

FIG. 4, shows an insert called a Size Large Sherpa Insert. Its specific arrangement is currently being used for a baby cloth diaper insert and it absorbs a maximum of ⅔-cup liquid waste. It commonly fits babies up to 16 months-potty training. In this particular example, center and arrange longest sides of three 3"×8" inner absorbing layers of synthetic microfiber terry 325-350 GSM (24) and two 3.5"×8" of 45% Organic Cotton/55% Hemp Fleece 9.6 oz. (24) parallel to the longest side of second inner absorbing layer 11"×6" of synthetic microfiber terry 325-350 GSM (30). Then, the three 3"×8" inner absorbing layers of synthetic microfiber terry 325-350 GSM (24) and two 3.5"×8" of 45% Organic Cotton/55% Hemp Fleece 9.6 oz. (24) are sewn at their edge to the 11"×6" synthetic microfiber terry 325-350 GSM second inner absorbing layer (30). Outer layer fabric #1 is 100% organic cotton sherpa 11"×6" weight 280 GSM (26) and is matched to 11"×6" synthetic microfiber terry 325-350 GSM second inner absorbing layer (30) with the three 3"×8" inner absorbing layers of synthetic microfiber terry 325-350 GSM (24) and two 3.5"×8" of 45% Organic Cotton/55% Hemp Fleece 9.6 oz. (24) sandwiched between. Then, on the top straight edge, outer layer fabric #1 100% organic cotton sherpa 11"×6" weight 280 GSM (26) is folded over ½ inch onto the 11"×6" synthetic microfiber terry 325-350 GSM second inner absorbing layer (30) with the three 3"×8" inner absorbing layers of synthetic microfiber terry 325-350 GSM (24) and two 3.5"×8" of 45% Organic Cotton/55% Hemp Fleece 9.6 oz. (24) sandwiched between and sewn to create a first finished edge. Next, a second finished edge at the pocket opening is created on the top straight edge. Outer layer fabric #2 100% organic cotton sherpa 11"×6" weight 280 GSM (32) is folded over ½ inch and sewn down. Outer layer fabric #1 100% organic cotton sherpa 11"×6" weight 280 GSM (26) and outer layer fabric #2 100% organic cotton sherpa 11"×6" weight 280 GSM (32) are matched and put together with the second inner absorbing layer 11"×6" synthetic microfiber terry 325-350 GSM (30) and three 3"×8" inner absorbing layers of synthetic microfiber terry 325-350 GSM (24) and two 3.5"×8" of 45% Organic Cotton/55% Hemp Fleece 9.6 oz. (24) sandwiched between them. All unfinished edges creating a U shape are sewn together while the first and second finished edges are left un-sewn. This will create the pocket opening.

Figure 5:
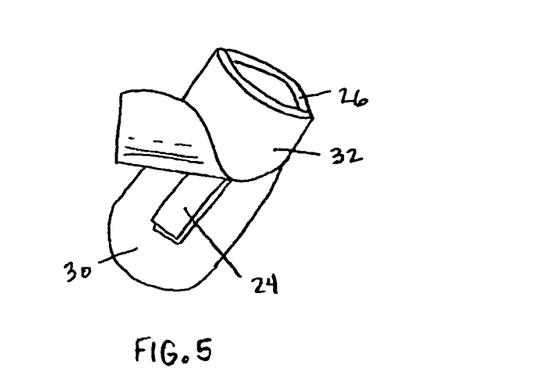
FIG. 5 shows an Organic Hemp Size Small baby cloth diaper insert that is capable of absorbing a maximum of ⅓ cup liquid waste that commonly fits babies from birth-16 months.

FIG. 5, shows an insert called a Size Small Hemp Insert. Its specific arrangement is currently being used for a baby cloth diaper insert and it absorbs a maximum of ⅓ cup liquid waste. It commonly fits babies up to 16 months. In this particular example, center and arrange longest sides of two 2.5"×8" inner absorbing layers made of synthetic microfiber terry 325-350 GSM (24) parallel to the longest side of second inner absorbing layer 11"×6" of synthetic microfiber terry 325-350 GSM (30). Then, the two 2.5"×8" inner absorbing layers made of synthetic microfiber terry 325-350 GSM (24) are sewn at their edge to the 11"×6" synthetic microfiber terry 325-350 GSM second inner absorbing layer (30). Outer layer fabric #1 is 45% Organic Cotton/55% Hemp Fleece 9.6 oz. 11"×6" (26) and is matched to 11"×6" synthetic microfiber terry 325-350 GSM second inner absorbing layer (30) with the two 2.5"×8" inner absorbing layers made of synthetic microfiber terry 325-350 GSM (24) sandwiched between. Then, on the top straight edge, outer layer fabric #1 45% Organic Cotton/55% Hemp Fleece 9.6 oz. 11"×6" (26) is folded over ½ inch onto the 11"×6" synthetic microfiber terry 325-350 GSM second inner absorbing layer (30) with two 2.5"×8" inner absorbing layers made of synthetic microfiber terry 325-350 GSM (24) sandwiched between and sewn to create a first finished edge. Next, a second finished edge at the pocket opening is created on the top straight edge. Outer layer fabric #2 45% Organic Cotton/55% Hemp Fleece 9.6 oz. 11"×6" (32) is folded over ½ inch and sewn down. Outer layer fabric #1 45% Organic Cotton/55% Hemp Fleece 9.6 oz. 11"×6" (26) and outer layer fabric #2 45% Organic Cotton/55% Hemp Fleece 9.6 oz. 11"×6" (32) are matched and put together with the second inner absorbing layer 11"×6" synthetic microfiber terry 325-350 GSM (30) and two 2.5"×8" inner absorbing layers made of synthetic microfiber terry 325-350 GSM (24) sandwiched between them. All unfinished edges creating a U shape are sewn together while the first and second finished edges are left un-sewn. This will create the pocket opening.

Figure 6:
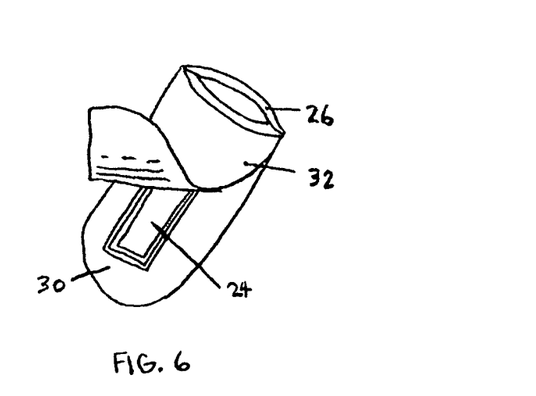
FIG. 6 shows an Organic Hemp Size Large baby cloth diaper insert that is capable of absorbing a maximum of ⅔ cup liquid waste that commonly fits babies 16 months-potty training.

FIG. 6, shows an insert called a Size Large Hemp Insert. Its specific arrangement is currently being used for a baby cloth diaper insert and it absorbs a maximum of ⅔ cup liquid waste. It commonly fits babies 16 months-potty training. In this particular example, center and arrange longest sides of three 3"×8" inner absorbing layers made of synthetic microfiber terry 325-350 GSM (24) parallel to the longest side of second inner absorbing layer 11"×6" of synthetic microfiber terry 325-350 GSM (30). Then, the three 3"×8" inner absorbing layers made of synthetic microfiber terry 325-350 GSM (24) are sewn at their edge to the 11"×6" synthetic microfiber terry 325-350 GSM second inner absorbing layer (30). Outer layer fabric #1 is 45% Organic Cotton/55% Hemp Fleece 9.6 oz. 11"×6" (26) and is matched to 11"×6" synthetic microfiber terry 325-350 GSM second inner absorbing layer (30) with the three 3"×8" inner absorbing layers made of synthetic microfiber terry 325-350 GSM (24) sandwiched between. Then, on the top straight edge, outer layer fabric #1 45% Organic Cotton/55% Hemp Fleece 9.6 oz. 11"×6" (26) is folded over ½ inch onto the 11"×6" synthetic microfiber terry 325-350 GSM second inner absorbing layer (30) with three 3"×8" inner absorbing layers made of synthetic microfiber terry 325-350 GSM (24) sandwiched between and sewn to create a first finished edge. Next, a second finished edge at the pocket opening is created on the top straight edge. Outer layer fabric #2 45% Organic Cotton/55% Hemp Fleece 9.6 oz. 11"×6" (32) is folded over ½ inch and sewn down. Outer layer fabric #1 45% Organic Cotton/55% Hemp Fleece 9.6 oz. 11"×6" (26) and outer layer fabric #2 45% Organic Cotton/55% Hemp Fleece 9.6 oz. 11"×6" (32) are matched and put together with the second inner absorbing layer 11"×6" of synthetic microfiber terry 325-350 GSM (30) and three 3"×8" inner absorbing layers made of synthetic microfiber terry 325-350 GSM (24) sandwiched between them. All unfinished edges creating a U shape are sewn together while the first and second finished edges are left un-sewn. This will create the pocket opening.

Alternative embodiments can also be possible and will not be limited what has been used in this present disclosure with regard to size, insert use, fabric configuration, and fabrics used.

The invention claimed is:

1. An absorbent insert for a diaper comprising:
    a pocket including an open end and a closed end, the open end defining a pocket opening;
    at least one first inner absorbing layer comprising an absorbent material;
    at least one second inner absorbing layer comprising an absorbent material; and
    an outer fabric layer comprising a fabric material;
    wherein the outer fabric layer is folded over the at least one second inner absorbing layer and secured to the at least one second inner absorbing layer adjacent the open end to form a 0.5-inch fabric flap on an inside of the pocket which defines a finished edge about the pocket opening, a remainder of the inside of the pocket comprising the at least one second inner absorbing layer;
    wherein the at least one first inner absorbing layer is sewn to the at least one second inner absorbing layer along edges of the at least one first inner absorbing layer; and
    wherein the at least one first inner absorbing layer is sandwiched between the outer fabric layer and the at least one second inner absorbing layer.

2. The absorbent insert of claim 1, wherein the at least one first inner absorbing layer and the at least one second inner absorbing layer comprise microfiber terry and/or hemp fleece.

3. The absorbent insert of claim 1, wherein the outer fabric layer comprises 100% organic cotton or a blend of organic cotton and hemp fleece.

* * * * *